United States Patent
Maiti et al.

(10) Patent No.: US 7,052,905 B1
(45) Date of Patent: May 30, 2006

(54) METHODS AND COMPOSITION FOR EXPRESSING MULTIPLE GENES IN PLANTS BY ALTERNATE SPLICING OF A POLYCISTRONIC MESSAGE

(75) Inventors: Indu Bhushan Maiti, Lexington, KY (US); Somnath Bhattacharyya, Barraekpore (IN)

(73) Assignee: University of Kentucky Research Foundation, Lexington, KY (US)

( * ) Notice: Subject to any disclaimer, the term of this patent is extended or adjusted under 35 U.S.C. 154(b) by 385 days.

(21) Appl. No.: 10/217,145

(22) Filed: Aug. 13, 2002

Related U.S. Application Data

(60) Provisional application No. 60/311,344, filed on Aug. 13, 2001.

(51) Int. Cl.
C12N 15/82 (2006.01)
C12N 5/10 (2006.01)
C12N 15/90 (2006.01)

(52) U.S. Cl. .................... 435/320.1; 435/468; 800/278

(58) Field of Classification Search ............ 435/320.1, 435/419, 468; 800/278, 279, 295, 298
See application file for complete search history.

(56) References Cited

OTHER PUBLICATIONS

I.B. Maiti et al., "Isolation and Expression Analysis of Peanut Chlorotic Streak Caulimovirus (PCISV) Full-Length Transcript (FLT) Promoter in Transgenic Plants", Biochemical and Biophysical Research Communications, vol. 244, (1998), pp. 440-444.

I.B. Maiti et al., "Promoter/leader deletion analysis and plant expression vectors with the figwort mosaic virus (FMV) full length transcript (FLt) promoter containing single or double enhancer domains", Transgenic Research 6, (1997), pp. 143-156.

I.B. Maiti et al., "Gene expression regulated by gene VI of caulimovirus: transactivation of downstream genes of transcripts by gene VI of peanut chlorotic streak virus in transgenic tobacco", Virus Research, vol. 57, (1998), pp. 113-124.

S. Bhattacharyya et al., Intron-mediated enhancement of gene expression in transgenic plants using chimeric constructs composed of the *Peanut chlorotic streak virus* (PCISV) promoter-leader and the antisense orientation of PCISV ORF VII (p7R), Plant, vol. 218, (2003), pp. 115-124.

I.B. Maiti et al., "Developing Genetically Engineered Disease, Pest and Herbicide Resistance in Tobacco", 46th Tobacco Chemists' Research Conference, Recent Advances in Tobacco Science, Highlights of Current Research on Tobacco and Tobacco Chemistry, Proceedings of a Symposium Presented at the 46th Meeting of the Tobacco Chemists' Research Conference, vol. 18, Sep. 27-30, 1992, pp. 45-68.

G. Wagner, "Improving Tobacco Through Metabolic Engineering: Promise and Obstacles", 46th Tobacco Chemists' Research Conference, Recent Advances in Tobacco Science, Highlights of Current Research on Tobacco and Tobacco Chemistry, Proceedings of a Symposium Presented at the 46th Meeting of the Tobacco Chemists' Research Conference, vol. 18, Sep. 27-30, 1992, pp. 3-43.

*Primary Examiner*—Ashwin Mehta
(74) *Attorney, Agent, or Firm*—McDermott Will & Emery LLP

(57) ABSTRACT

The present invention provides a method and composition for expression of multiple genes from a polycistronic message in transgenic plants using genetic elements derived from the peanut chlorotic streak caulimovirus promoter-leader sequence and antisense sequence of PC1SV ORF VII. Also provided are compositions and methods for intron-mediated enhanced and regulated expression of genes in transgenic plants.

21 Claims, 10 Drawing Sheets

Figure 1
Monocistronic construct
pP9Lp7RG
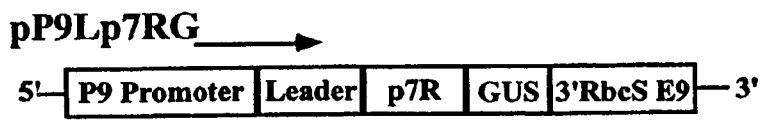
Dicistronic construct
pP9LGp7RC
pP9Lp7RGp7RC
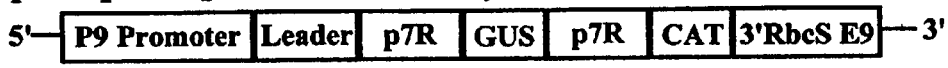
Tricistronic construct
pP9LGfp7RGp7RC
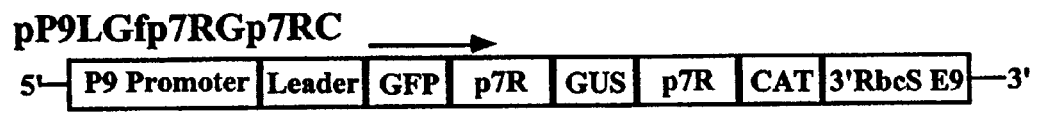
pP9Lp7RGfp7RGp7RC
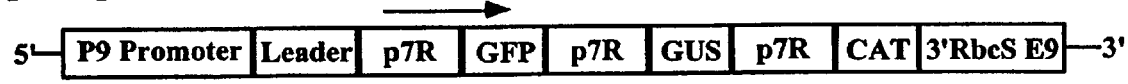

Figure 2

SEQ ID NO. 1: Length 346 nt

ACACGATCGA GAAGACACGG CCATTTGGAC GATCATTTGA GAGTCTAAAA

50

GAACGAGTCT TGTAATATGT TTTTCAGAGA TAATAAAATT ATGATATTCA

100

GTTATTCTAT GAGTCACTAG AAACCTTTCA AGGTTATAGC TAGTAGAGGT

150

ATACTGTTAT AGAAATAGCA GATTTCCAGA TTTCACTGAA GAGCGCGTCA

200

GGAACTCGCA    CGACTGAAGC    CAGGTGGGCG    TTTATGTGCT

GGAGGCCGCA    250

AGCGTTGTGA AAGGAAGGGC TATAGATATA TCAGGTATAT TTCGAACGCT

300

GTAATCTTGA AGTTTTAAAT CATAGAATTT TCTCTGAATA AGAAAT

SEQ ID NO. 2: Length: 432 nt

CTAGACATTA TAGATAGCTT TCTGGATGTC TTTATAAAAC ATGTTGATTC
50

TGGGGATAAC TATGTTATCT AAGATCAAAT GTTTACTAGT TATCTTATAA
100

TCAAAATTTT CTAAGAAATC AATTCCTAAC AAAACTTTTT TCTTTTCTGG
150

GTTTCTACGA TTATCTACTG GTATTTCAAC ATTTATCTTT ATGTCTTTTG
200

TAAAGATTAT TTCTACACTG GCTAACTTTT CATTGGTGAC TTCCTCACCA
250

TCATATGTTA TATATGATAT TGGATTTCCT CCATCATATA TCTCATATGT
300

TAGATCCTTG GAGATGTGGG ATGAACATGC TCCTGTGTCT ATTAGTATGA
350

TGCATAGCTG TTTATTAACA TATGCAATAA CATGATATTG ACTATAATTT
400

TGTTCGTCTA ATTTTATCTG ATAGGATTTC AT
432

Figure 4 A and 4 B
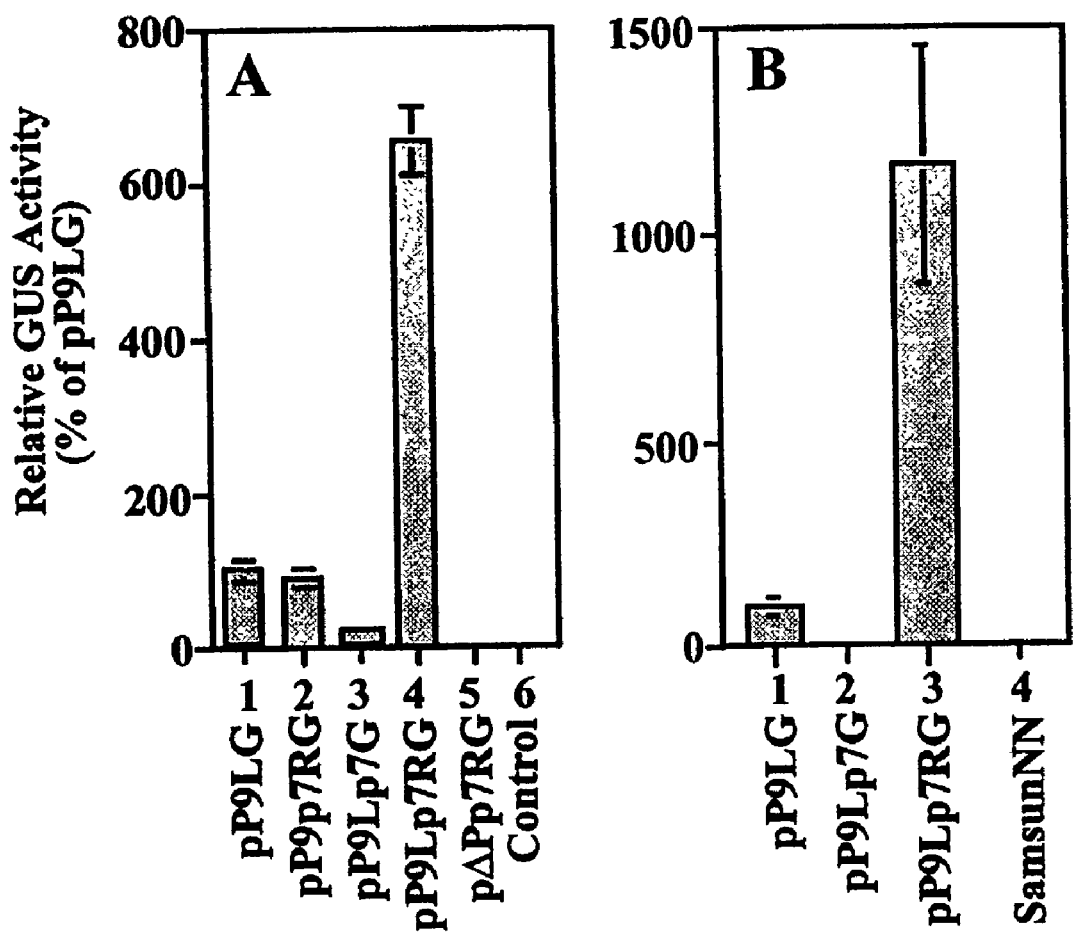

Figure 5 A and 5 B:
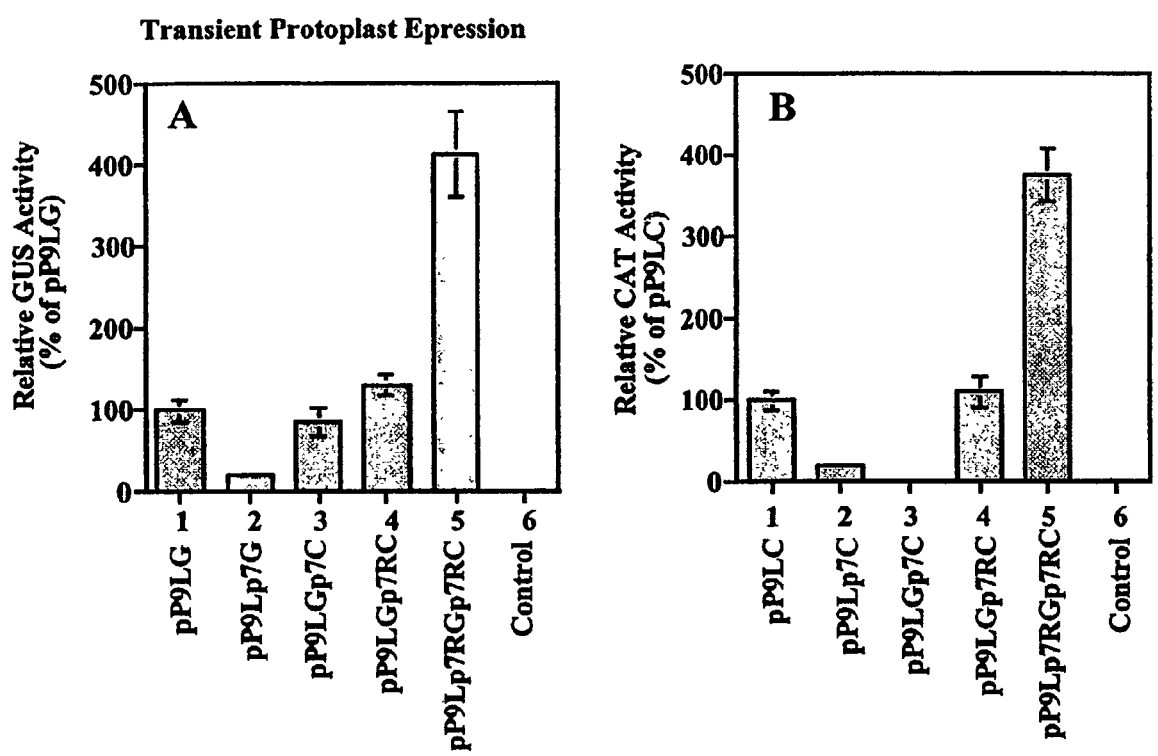

Figure 6 A and 6 B:
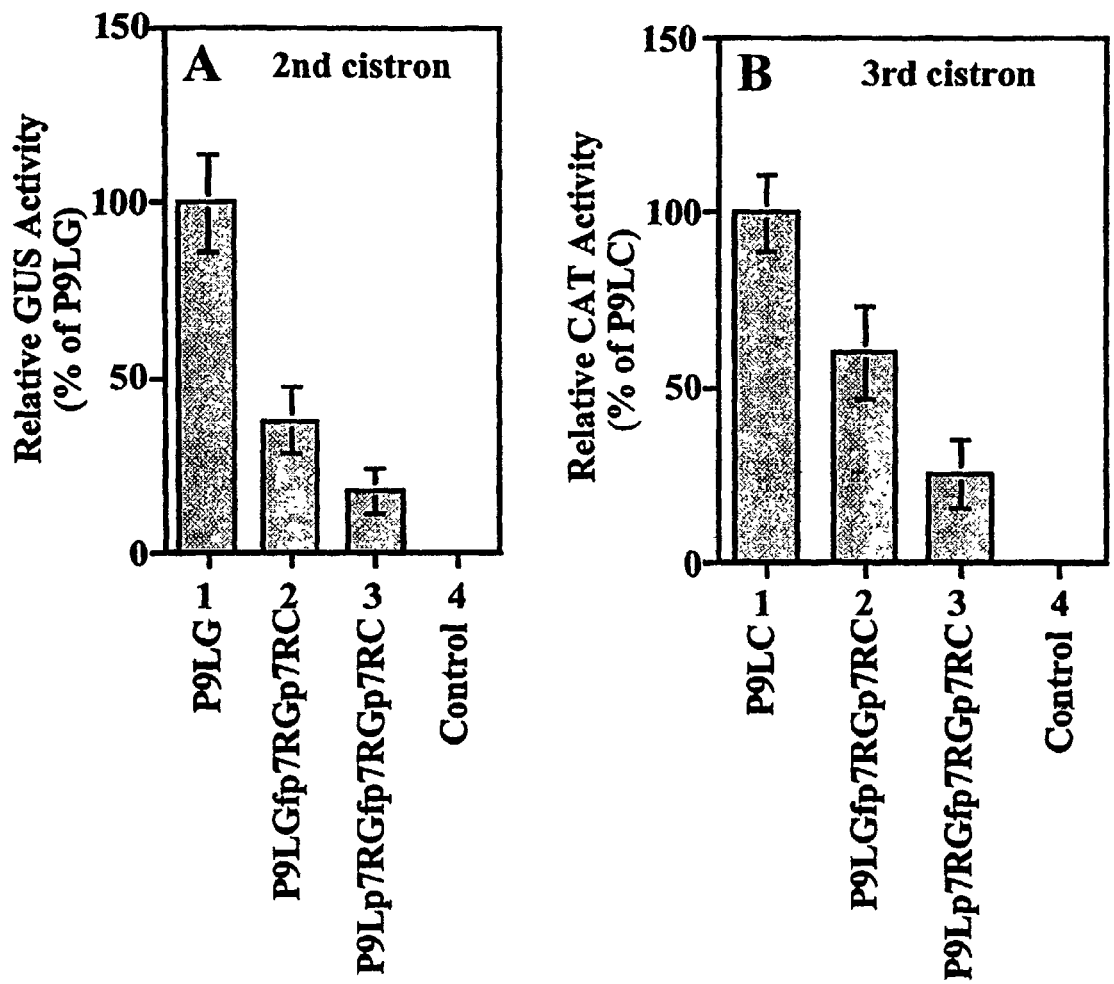

Figure 7 A, 7B, 7C and 7D
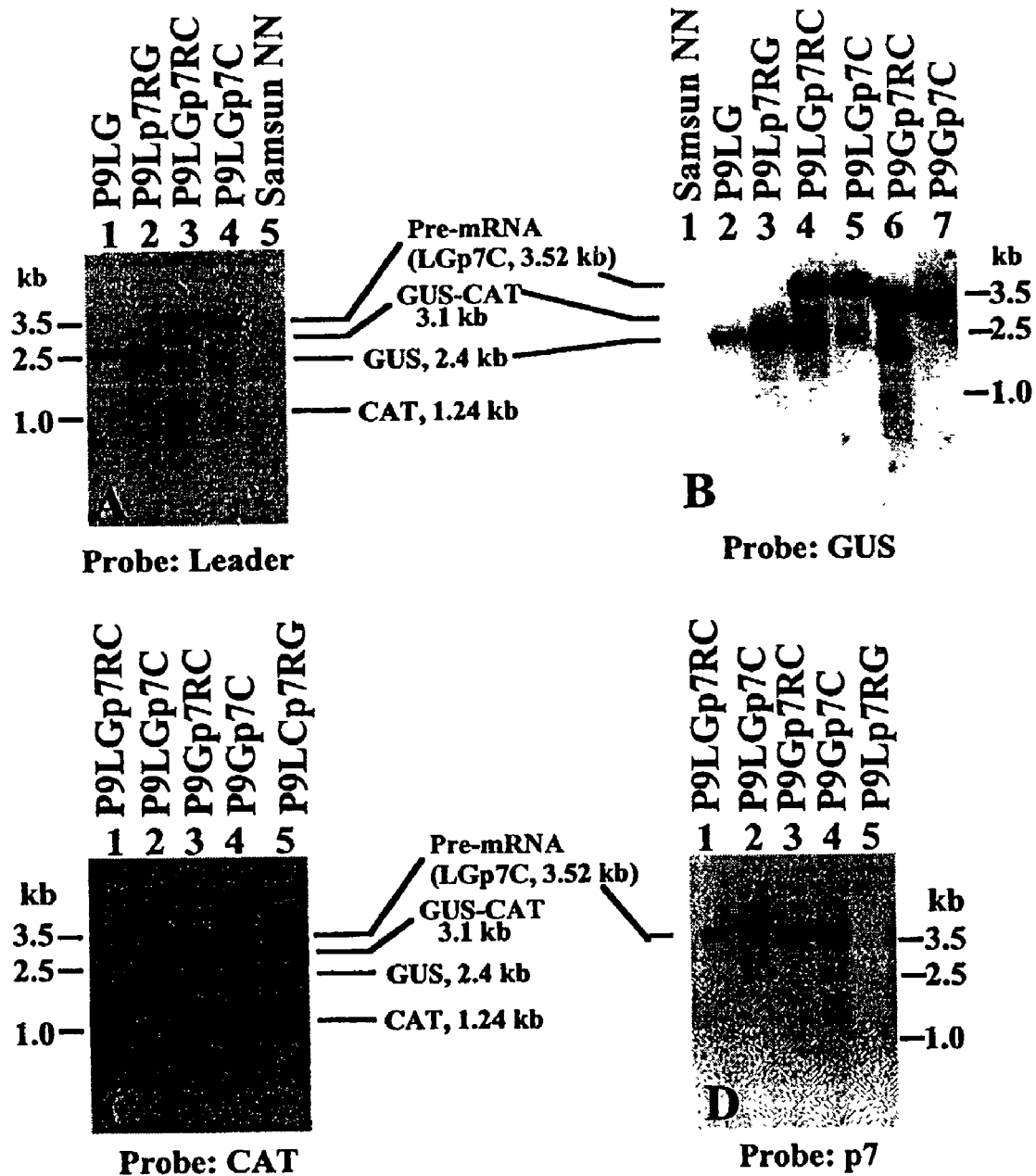

Figure 8 A and 8B,

SEQUENCE LISTING

```
<160> NUMBER OF SEQ ID NOS: 2

<210> SEQ ID NO 1
<211> LENGTH: 346
<212> TYPE: DNA
<213> ORGANISM: Artificial sequence
<220> FEATURE:
<223> OTHER INFORMATION: Derived from peanut chlorotic streak virus

<400> SEQUENCE: 1
acacgatcga gaagacacgg ccatttggac gatcatttga gagtctaaaa gaacgagtct      60
tgtaatatgt ttttcagaga taataaaatt atgatattca gttattctat gagtcactag     120
aaacctttca aggttatagc tagtagaggt atactgttat agaaatagca gatttccaga     180
tttcactgaa gagcgcgtca ggaactcgca cgactgaagc caggtgggcg tttatgtgct     240
ggaggccgca agcgttgtga aaggaagggc tatagatata tcaggtatat ttcgaacgct     300
gtaatcttga agtttaaat catagaattt tctctgaata agaaat                     346

<210> SEQ ID NO 2
<211> LENGTH: 432
<212> TYPE: DNA
<213> ORGANISM: Artificial sequence
<220> FEATURE:
<223> OTHER INFORMATION: Derived from peanut chlorotic streak virus

<400> SEQUENCE: 2
ctagacatta tagatagctt tctggatgtc tttataaaac atgttgattc tggggataac      60
tatgttatct aagatcaaat gtttactagt tatcttataa tcaaaatttt ctaagaaatc     120
aattcctaac aaaactttt tcttttctgg gtttctacga ttatctactg gtatttcaac      180
atttatcttt atgtcttttg taaagattat ttctacactg gctaactttt cattggtgac     240
ttcctcacca tcatatgtta tatatgatat tggatttcct ccatcatata tctcatatgt     300
tagatccttg gagatgtggg atgaacatgc tcctgtgtct attagtatga tgcatagctg     360
tttattaaca tatgcaataa catgatattg actataattt tgttcgtcta attttatctg     420
ataggatttc at                                                         432
```

METHODS AND COMPOSITION FOR EXPRESSING MULTIPLE GENES IN PLANTS BY ALTERNATE SPLICING OF A POLYCISTRONIC MESSAGE

This application claims priority to U.S. Application No. 60/311,344, filed Aug. 13, 2001.

FIELD OF THE INVENTION

The invention relates to a gene splicing system for use in plants. More particularly, the invention relates to an expression system for constitutive expression of multiple genes as a polycistronic unit in transgenic plants.

BACKGROUND OF THE INVENTION

The expression of useful foreign traits in plants is a major focus in plant biotechnology. Introduction of heterologous genes of interest into plant cells generates the desired qualities in the plants of choice (Maiti and Hunt, 1992; Wagner, 1992). Plant biotechnology is leading a rapid progress in production of economically valuable germplasm with improved characteristics or traits such as insect resistance, virus resistance, fungal resistance, herbicide resistance, bacterial or nematode pathogen resistance, cold or drought tolerance, improved nutritional value, seed oil modification, delayed ripening of fruits, and male sterility, to name a few. These germplasms provide an enhanced development in breeding programs for crop improvement as well as a better understanding of gene regulation and organization in transgenic plants.

Plant metabolic engineering is the application of genetic engineering methods to modify the nature of chemical metabolites in plants. However, for metabolic engineering, multiple genes must inserted into a single cell. Thus, there is a need for an efficient system for introducing multiple genes into single plant cells and obtaining translation of the mRNAs transcribed from the inserted genes.

SUMMARY OF THE INVENTION

In one aspect of the invention there is provided an expression cassette comprising a plant promoter operatively linked to SEQ ID NO: 1 or a functional equivalent thereof, which is operatively linked to SEQ ID NO: 2 or a functional equivalent thereof. In a preferred embodiment the expression cassette further comprises a polynucleotide sequence encoding a polypeptide or peptide operatively linked downstream of SEQ ID NO. 2 or the functional equivalent thereof. In a most preferred embodiment, the promoter is a P9 promoter.

In another aspect of the invention there is provided a polycistronic expression cassette comprising a 5'-plant promoter operatively linked to SEQ ID NO: 1 or a functional equivalent thereof, which is operatively linked to a first nucleotide sequence encoding a first polypeptide, which is operatively linked to SEQ ID NO: 2 or a functional equivalent thereof, which is operatively linked to a second nucleotide sequence encoding a second polypeptide, which is operatively linked to a termination sequence. In a preferred embodiment, the second polynucleotide sequence is operatively linked downstream to SEQ ID NO. 2 or a functional equivalent thereof, which is operatively linked downstream to a third nucleotide sequence encoding a third polypeptide.

In yet another embodiment of the invention there is provided a polycistronic expression cassette comprising a plant promoter operatively linked to SEQ ID NO. 1 or a functional equivalent thereof, which is operatively linked to SEQ ID NO. 2 or a functional equivalent thereof, which is operatively linked to a first polynucleotide encoding a first polypeptide, which is operatively linked downstream to SEQ ID NO. 2 or a functional equivalent thereof, which is operatively linked downstream to a second polynucleotide encoding a second polypeptide.

In another aspect of the invention there is provided a transgenic plant, transgenic plant tissue, transgenic plant cell, or transgenic seed comprising the an expression cassette of the invention.

In another aspect of the invention, there is provided a method of providing enhanced or regulated expression of one or more peptides or polypeptides in a plant, plant cells, plant tissue, or seeds comprising:

transforming the plant, plant cells, plant tissue, or seeds with an expression cassette of the invention; and expressing the polypeptide or polypeptides encoded by the expression cassette.

BRIEF DESCRIPTION OF THE DRAWINGS

FIG. 1 is a schematic map of mono-, di-, and tri-cistronic-expression constructs. General structures of the plasmids pP9Lp7RG (mono-cistronic construct), pP9LGp7RC and pP9Lp7RGp7RC (di-cistronic construct), and pP9LGfp7RGp7RC and pP9Lp7RGfp7RGp7RC (tri-cistronic construct) are shown. These constructs are assembled with PC1SV leader and p7R as intervening sequence in the order indicated. The arrows show the direction of transcripts of Genes (GFP, GUS and CAT gene) driven by the PC1SV FLt promoter (P9).

FIG. 2 is the DNA sequence of PC1SV leader (SEQ ID NO: 1 (corresponding PC1SV genomic coordinates 6078 to 6423).

FIG. 3 is the antisense DNA sequence of PC1SV gene VII (Designated as p7R) (SEQ ID NO: 2)

FIGS. 4A and 4B are expression analyses of monocistronic constructs in protoplast transient expression experiments (4A) and stably transformed transgenic plants (4B). The level of GUS expression is presented as percent activity of pP9LGUS. The protoplast assay-data (FIG. 4A) are means of five independent experiments for each construct; the average GUS activity is presented for each construct with standard deviation. For the transgenic plant assay, (FIG. 4B) about 10 to 12 independent lines were developed for each construct; relative GUS activity is presented for each construct with standard deviation.

FIGS. 5A, 5B, 5C and 5D are expression analyses of dicistronic constructs. Expression analysis of dicistronic constructs in protoplast transient expression experiments is shown in FIGS. 5A and 5B. The results are presented as average GUS or CAT activity with standard deviation generated from five independent experiments. Expression analysis of dicistronic constructs in transgenic plants is shown in FIGS. 5C and 5D. About 12 independent transgenic lines were developed for each construct. The average GUS ($1^{st}$ cistron) or CAT activity ($2^{nd}$ cistron) is presented with standard deviation.

FIGS. 6A and 6B are expression analyses of tricistronic constructs. Expression analysis of GUS ($2^{nd}$ cistron) and CAT ($3^{rd}$ cistron) from tricistronic constructs in protoplasts transient expression experiments are shown.

FIGS. 7A, 7B, 7C and 7D are Northern analysis of transgenic plants developed for the mono- and dicistronic constructs.

DETAILED DESCRIPTION OF THE INVENTION

Figures 5C, 5D:
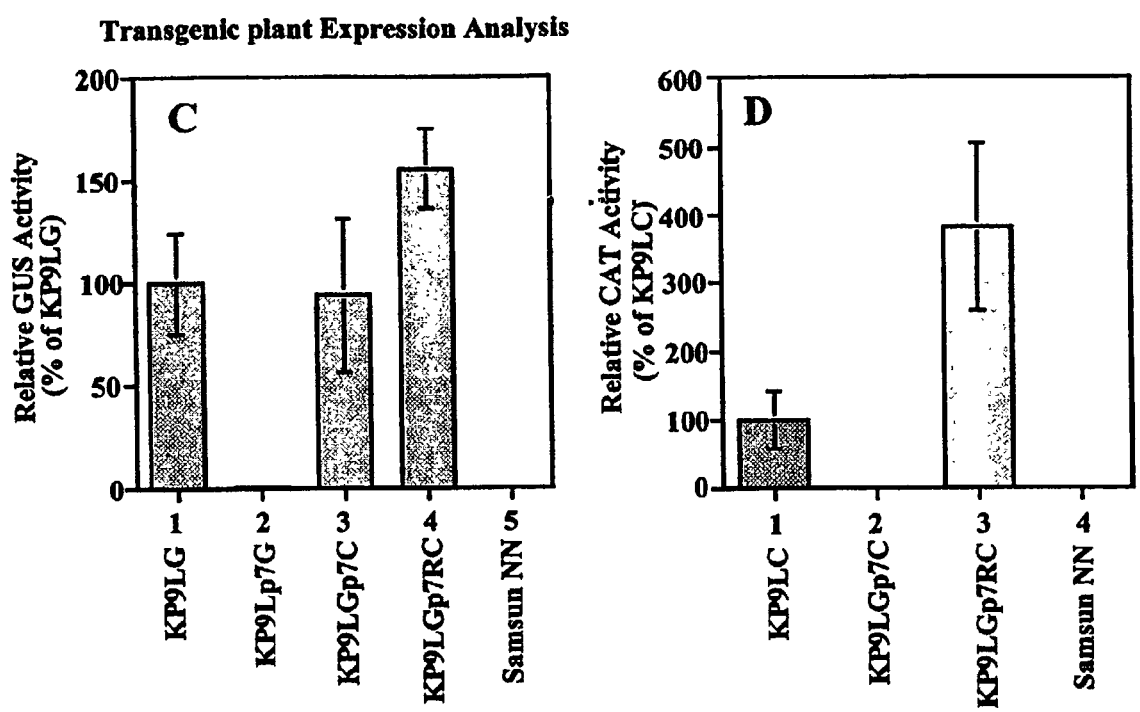

For modification of plants to have multiple desired traits through metabolic engineering it is necessary to introduce several foreign genes into plants. The expression of genes may need to be coordinated and regulated in a predicted way. The present invention provides an expression system for the constitutive expression of multiple genes as a polycistronic unit in transgenic plants using a peanut chlorotic streak virus (PC1SV) leader sequence and an antisense strand of a PC1SV gene VII (denoted herein as p7R) as intervening sequences, which together compose a polycistronic unit. The regulated expression of the polycistronic mRNA is mediated by alternate splicing. This novel splicing system will be very useful for studying the mechanism of intron splicing in plants.

The expression system for constitutive expression of multiple genes as a polycistronic unit in transgenic plants is based on a surprising discovery concerning certain DNA fragments derived from peanut chlorotic streak virus (PCISV). It has been discovered that these DNA fragments have distinct splicing activity in plants. A polycistronic expression cassette has been developed that is composed of peanut chlorotic streak virus (PC1SV) full-length transcript promoter-leader sequence and antisense sequence of PC1SV gene VII (denoted as p7R) as intervening sequence; and GFP, GUS and CAT as reporter genes. Any gene or polynucleotide sequence, such as a polynucleotide sequence encoding an antisense transcript, for example, may be inserted in the construct in place of the marker genes. Also, it is not essential that the chlorotic steak virus promoter be used in the constructs of the invention, although the P9 promoter is preferred. Other plant promoters may be substituted for the P9 promoter.

Alternatively, the expression cassette may contain a sequence that hybridizes under high stringency conditions to the peanut chlorotic streak virus (PC1SV) promoter-leader sequence and together with p7R has alternate splicing activity in plants and/or a sequence that hybridizes under high stringency conditions to p7R and has alternate splicing activity in plants, i.e., sequences that are functionally equivalent to the chlorotic streak virus (PC1SV) promoter-leader sequence or p7R sequence. An example of highly stringent wash conditions is 0.15 M NaCl at 72° C. for about 15 minutes. An example of stringent wash conditions is a 0.2×SSC wash at 65° C. for 15 minutes (See, Sambrook et al. (1989) Molecular Cloning—A Laboratory Manual (2nd ed.) Vol. 1–3, Cold Spring Harbor Laboratory, Cold Spring Harbor Press, N.Y., for a description of SSC buffer and description of stringency conditions for nucleic acid hybridization). Often, a high stringency wash is preceded by a low stringency wash to remove background probe signal. An example of a medium stringency wash for a duplex (e.g., of more than 100 nucleotides), is 1×SSC at 45° C. for 15 minutes. An example of low stringency wash for a duplex (e.g., of more than 100 nucleotides), is 4–6×SSC at 40° C. for 15 minutes. In general, a signal to noise ratio of 2× (or higher) than that observed for an unrelated probe in the particular hybridization assay indicates detection of a specific hybridization. Nucleic acids which do not hybridize to each other under stringent conditions are still substantially identical if the polypeptides which they encode are substantially identical. This occurs, for example, when a copy of a nucleic acid is created using the maximum codon degeneracy permitted by the genetic code.

The PC1SV full-length transcript promoter-leader sequence and the antisense sequence of PC1SV gene VII act as introns in this process and are involved in alternate splicing of the polycistronic units. The system has been tested both in transient protoplast expression experiments and in stably transformed transgenic plants.

The intron mediated enhanced expression of genes is also demonstrated with the use of this system. The efficient translation of polycistronic mRNAs has value in plant metabolic engineering.

The present invention provides plant expression vectors and intermediate transforming vectors containing the expression cassette of the invention. The polycistronic expression cassette is useful for directing and expressing foreign genes of interest, e.g., pathogen resistance genes, genes encoding metabolic proteins, gene encoding stress resistance factors, etc., in plants to confer useful properties to those transgenic plants, such as pathogen or stress resistance, for example. These vectors are useful for both direct DNA uptake by isolated protoplasts and Ti plasmid-mediated gene transfer. Thus, the invention is applicable to plant genetic engineering in general.

For example, the polycistronic expression cassette constructs of the invention may be included in an intermediate plant transformation plasmid which has a region of homology to an *Agrobacterium tumefaciens* gene vector, and an *Agrobacterium tumefaciens* T-DNA border region.

The present invention also provides plant transformation vectors comprising a disarmed *Agrobacterium tumefaciens* plant tumor-inducing plasmid and the polycistronic expression cassette. The expression cassette preferably encodes one or more heterologous polypeptide or peptides.

The polycistronic expression cassette, and plasmids and vectors of the invention containing the polycistronic expression cassette can be used to generate stable transgenic plants or transform plant protoplasts. Methods for transforming plant protoplasts and generating transgenic plants are well known in the art of plant molecular engineering. For generating transgenic plants or plant protoplasts, the polycistronic expression cassette encodes at least one polypeptide of interest. In one embodiment of the invention, the polycistronic expression cassette may encode multiple copies of a single polynucleotide sequence.

The polycistronic expression cassettes of the invention can be used to generate transgenic plants in any type of plant, i.e., monocots or dicots. Preferably, transgenic plants of the invention are crop plants, such as tobacco, hemp, or food crops, such as tomato, corn, soy, wheat, rice, etc. Transgenic plants of the invention may also be flowering plants, such as carnations, roses, and the like. The skilled practitioner, using methods known in the art, can readily transform any plant type using the isolated DNA molecules and vectors of the invention.

The polycistronic expression cassettes of the present invention can be used to generate transgenic plants, seeds or protoplasts, and may be used to drive expression of a gene or genes of interest in any plant tissue, e.g., roots, stems, leaves, flowers, stems, pollen, or seeds.

The present invention is illustrated by the following examples, but is not intended to be limited thereby.

EXAMPLE 1

Expression of Monocistronic Constructs in Protoplasts and Transgenic Plants

The effect of PC1SV leader and p7R sequence on the expression of downstream gene in the monocistronic construct pP9Lp7RG was evaluated. Results of protoplast transient expression experiments and in stably transformed transgenic plants are shown in FIGS. 4A and 4B respectively. The GUS expression level in pP9LG where GUS gene (denoted as G) is under PC1SV FLt promoter (Maiti and Shepherd 1988; denoted as P9) with its leader sequence (denoted as L) was considered as 100% as full activity (FIG. 4A, lane 1; FIG. 4B, lane 1). In the construct pP9p7RG, where leader sequence was substituted with p7R sequence the GUS expression level was about 93% of full activity (FIG. 4A, lane 2). The GUS expression level in pP9Lp7RG is about 6.5 to 11.6 times higher than that with pP9LG shown in protoplast assay (FIG. 4A lane 4) and transgenic plant assay (FIG. 4B lane 3) respectively. Our results clearly showed that the presence of both PC1SV leader and p7R sequence are required for high expression of down stream gene. The plasmid, pPΔp7RG, where PC1SV promoter was replaced with p7R sequence, gave no GUS expression (FIG. 4A, lane 5) indicating that p7R sequence has no promoter activity in plants. The p7R acts as an intron shown in Example no. 4.

The p7R sequence is involved in intron-mediated enhanced expression of downstream gene. The plasmid pP9Lp7G, where GUS gene is fused with PC1SV gene VII (denoted as p7) following the leader sequence, gave about 22% of full activity (FIG. 4A, lane 3) in protoplast assay and less than 3% of full activity in transgenic plant assay (FIG. 4B, lane 2). It is clearly shown that the p7R not p7 in conjunction with PC1SV leader is involved in enhanced expression of chimeric gene in plants.

EXAMPLE 2

Expression of Dicistronic Constructs in Protoplasts and Transgenic Plants

The influence of PC1SV leader and p7R sequence were also analyzed for the dicistronic constructs, pP9LGp7RC and pP9Lp7RGp7RC, assayed both in a protoplast transient expression experiments (FIGS. 5 A and 5 B) and in stably transformed transgenic plants (FIGS. 5 C and 5 D). The expression of GUS gene in pP9LG (FIG. 5A, lane 1) or CAT gene in pP9LC (FIG. 5B, lane 1) under control of the PC1SV FLt promoter (Maiti and Shepherd 1988) and leader was considered 100% as full activity.

In a dicistronic construct, pP9LGp7RC, with p7R as an intergenic region between the GUS and CAT genes, the expression of GUS (as $1^{st}$ cistron) and CAT (as $2^{nd}$ cistron) was 130% (FIG. 5A, lane 4) and 110% (FIG. 5B, lane 4) of full activity, respectively. In construct, pP9Lp7RGp7RC, where p7R is located between the leader and first cistron and between the first and second cistrons, the expression level of GUS as $1^{st}$ cistron and CAT as $2^{nd}$ cistron were 414% (FIG. 5A, lane 5) and 377% (FIG. 5 B, lane 5) of full activity, respectively. As control, dicistronic construct pP9Lp7G (FIG. 5 A, lane 2) or pP9Lp7C (FIG. 5 B, lane 2), where GUS or CAT gene fused with p7 following leader showed about 20% of full activity.

In the tricistronic construct, pP9LGp7C, the expression level of GUS as $1^{st}$ cistron and of CAT as $3^{rd}$ cistron were about 87% (FIG. 5 A, lane 3) and 0.20 (FIG. 513, lane 3), respectively, of full activity.

A similar expression profile for the dicistronic construct, P9LGp7RC, was documented in stably transformed transgenic plants for the GUS gene (as $1^{st}$ cistron) and CAT (as $2^{nd}$ cistron); the expression levels were 155% (FIG. 5C, lane 4) and 383% (FIG. 5 D, lane 3) of full activity, respectively.

A coordinated role of PC1SV leader and p7R sequence is necessary to obtain high expression of dicistronic units.

EXAMPLE 3

Expression of Tricistronic Constructs in Protoplasts

The expression pattern of the following tricistronic constructs: P9LGf-p 7RGp7RC and P9Lp7RGfp7RGp7RC was analyzed in protoplasts in transient expression the mono- and dicistronic constructs shown in the previous examples. The level of expression in P9LGf-p7RGp7RC of $2^{nd}$ cistron (GUS in this case) and $3^{rd}$ cistron (CAT in this case) was 38% and 60% of full activity, respectively (FIG. 6 A, lane 2 and FIG. 6 B, lane 2, respectively). In construct, P9Lp7RGfp7RGp7RC, the level of expression of GUS as $2^{nd}$ cistron and CAT as $3^{rd}$ cistron was 18% and 25% of the full activity respectively (FIG. 6 A, lane 3 and FIG. 6 B, lane 3), respectively.

These results clearly demonstrate that the disclosed way of using a PC1SV leader sequence and p7R sequence provides a novel strategy in composing chimeric polycistronic constructs that enable regulation of the expression of multiple genes from a poly cistronic unit in transgenic plants. The PC1SV promoter-leader and p7R sequence can be used in developing various genetic switches.

EXAMPLE 4

Molecular Analysis of Gene Expression and Alternate Splicing: Northern Blot and Splicing Events Total RNA was isolated from 4-week old seedlings (R1 progeny, $2^{nd}$ generation) of untransformed and transformed plants developed for the following constructs: P9LG (general structure PC1SV FLt promoter-leader-GUS), P9Lp7RG and P9LGp7RC. Hybridization analysis of total RNA was performed using $^{32}$P-labeled probes specific for leader, GUS, CAT and p7 sequence. The results are shown in FIG. 7.

Plants developed for KP9LG showed an expected band of ~2.4 kb (predicted general structure L-GUS-polyA) when probed with either $^{32}$P-leader (FIG. 7A, lane 1) or $^{32}$P-GUS (FIG. 7B, lane 1).

Total RNA from plants developed with dicistronic construct, P9LGp7RC, was probed separately with $^{32}$P-leader (FIG. 7A, lane 3), 32 P-GUS (FIG. 7B, lane 4), 32 P-CAT (FIG. 7 C, lane 1) and $^{32}$P-p7 (FIG. 7D, lane 1). The RNA probed with $^{32}$P-leader showed two major transcripts of ~2.33 kb size (predicted general structure: Lo-GUS-polyA; Lo, part of the leader), and 1.2 kb size (predicted general structure: Lo-CAT-polyA) and two minor transcripts of ~3.52 kb size (predicted general structure: Lo-GUS-p7R-CAT-polyA) and a ~3.09 kb size (predicted general structure: Lo-GUS-CAT-polyA) (FIG. 6A, lane 3). The total RNA of P9LGp7RC plants probed with $^{32}$P-GUS showed a major transcript of ~2.4 kb (predicted general structure: Lo-GUS-polyA) and two other transcripts of ~3.52 kb and 3.1 kb (FIG. 7B, lane 4). When probed with $^{32}$P-CAT, plants developed with P9LGp7RC showed a major transcript of ~1,2 kb (predicted general structure; Lo-CAT-polyA) (FIG. 7 C, lane 1) that was also shown when probed with $^{32}$P-Leader (FIG. 6A, lane 3). There were also two very minor bands of transcripts of ~3.52 kb size (predicted general structure: Lo-GUS-p7R-CAT-polyA) and 3.09 kb size (predicted general structure: Lo-GUS-CAT-polyA), FIG. 3C, lane 1). When probed with $^{32}$P-p7 it showed a single band of size ~3.52 kb (predicted general structure (Lo-GUS-p7R-CAT-polyA) and that is the pre-mRNA (FIG. 7D, lane 1). Transcript analysis clearly showed that the splicing of the pre-mRNA is responsible for expression of genes from this chimeric construct. The p7R sequence is mostly spliced out. The PC1SV leader and p7R are involved in coordinating the splicing process.

Total RNA from plants developed with P9Lp7RG (general structure: P9 promoter-leader-p7R-GUS) showed a major transcript of ~2.33 kb when probed with either $^{32}$P-leader (FIG. 7A, lane 2) or $^{32}$P-GUS (FIG. 7B, lane 3). This transcript with predicted general structure Lo-GUS-polyA was not detected when probed with $^{32}$P-p7 (FIG. 7B, lane 5), indicating that p7R sequence is spliced out during RNA processing.

Several constructs designed with or without leader and p7 sequences were analyzed along with the test constructs. Total RNA from plants developed with the construct P9LGp7C (general structure: P9-leader-GUS-p7-CAT) gave a major transcript of 3.52 kb when probed with either $^{32}$P-leader (FIG. 7A, lane 4), $^{32}$P-GUS (FIG. 7B, lane 5), $^{32}$P-CAT (FIG. 7C, lane 2) or $^{32}$P-p7 (FIG. 7D, lane 2). This result indicates that p7R, but not p7 is involved in splicing process. Plants developed with P9 Gp7C (general structure P9-GUS-p7-CAT) showed a single major transcript of ~3.18 kb when probed with either $^{32}$P-GUS (FIG. 7B, lane 7), $^{32}$P-CAT (FIG. 7C, lane 4) or $^{32}$P-p7 (FIG. 7D, lane 4). Total RNA from plants developed with P9 Gp7RC (general structure P9 promoter-GUS-p 7R-CAT) when probed with $^{32}$P-GUS showed two major transcripts of ~2.05 kb (predicted general structure GUS-polyA) and ~3.18 kb (predicted general structure GUS-p7R-CAT-polyA). The larger 3.18 kb transcript was also detected when probed with either $^{32}$P-CAT (FIG. 7C, 3) or $^{32}$P-p7 (FIG. 7D, lane 3). It suggests that GUS m-RNA is processed from the pre-mRNA and p7R is spliced out, but CAT-mRNA is not processed. As negative control, total RNA from untransformed control plants (Samsun NN) gave no transcript when probed with either $^{32}$P-leader (FIG. 7A, lane 5) or $^{32}$P-GUS (FIG. 7B, lane 1). Taking all these results together, Northern analysis established that leader and p7R sequences are responsible for the proper splicing of these chimeric test constructs described in present invention.

EXAMPLE 5

Identification of Splicing Sites Through RT PCR and DNA Sequencing

RT-PCR analysis was performed using total RNA isolated from plants developed for the construct, P9Lp7RG, using the following primers pairs: Forward primer A, 5'-end of leader sequence including XhoI site, and Reverse primer B from the 5'-end of 3'rbcS-terminator, relative position of PCR-primer (A and B) is pointed out by an arrow in FIG. 8 A. RT-PCR analysis showed a band of size ~2.2 kb (general structure Leader-GUS) (FIG. 8 B, lane 1) as expected from the Northern results. DNA sequence analysis of this RT-PCR fragment showed that most of the p7R sequence was spliced out taking 60 nucleotides (nt) from the 3'-end of the leader sequence at the 5' splice site, but keeping 9 nt of its own at its 3'-end. This process followed the conscientious GT/AG rule for splicing.

Figure 8:
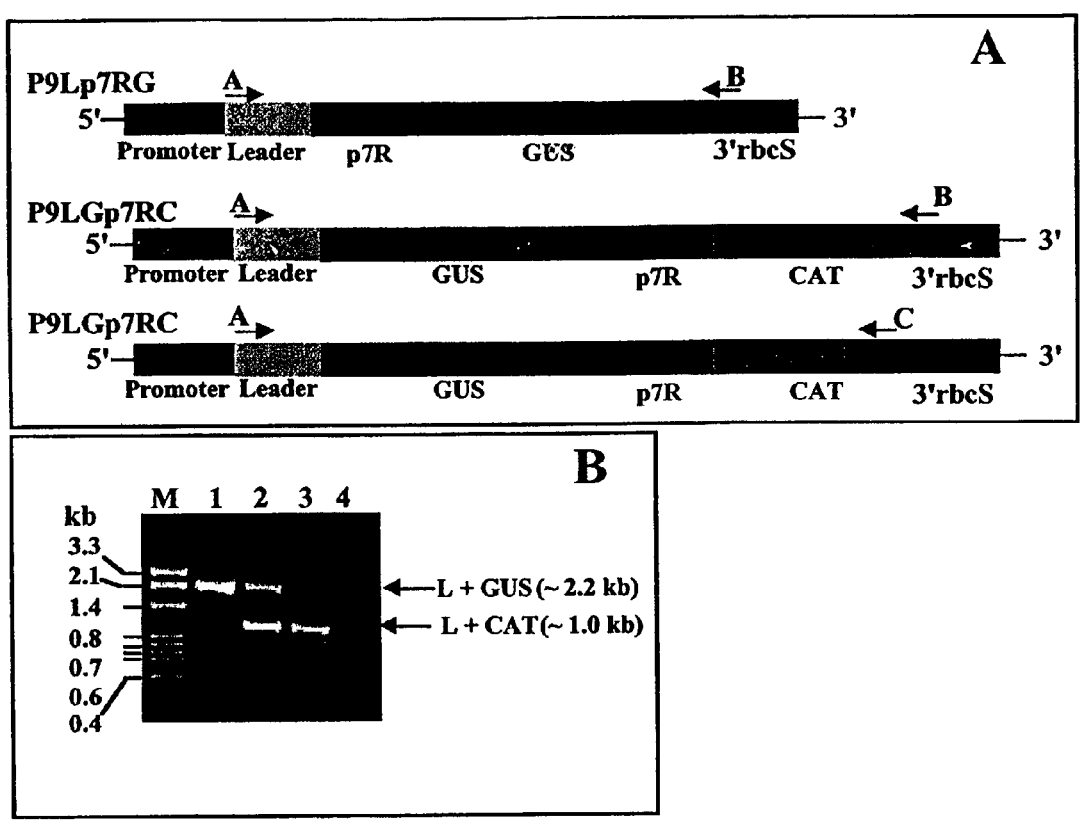
FIGS. 8A, 8B are RT-PCR analyses. RT-PCR analyses of total RNA from plants developed for mono- and dicistronic constructs are presented. General structure of constructs, relative position of forward and reverse PCR primers (A, B and C) indicated by arrows (FIG. 8A) are shown. RT-PCR analysis displayed (FIG. 8B) for p(Lp7RG (lane 1), P9 Gp7RC (lane 2 and 3), Samsun NN as untransformed control (lane 4) and DNA size marker (lane M) are shown.

Similarly, total RNA isolated from plants transformed with dicistronic construct, P9 Gp7RC, was subjected to RT-PCR analysis using the following primer pairs: A and B for one set, and A and reverse primer (C), 3'-end of CAT sequence for another set. RT-PCR analysis with primer A and B showed two major bands: ~2.2 kb (general structure leader-GUS) and ~1.0 kb (general structure (leader-CAT) fragments (FIG. 8 B, lane 2). Sequencing of the ~1.0 kb fragment containing CAT also showed the same 5' and 3' splicing sites at the 3'-end of leader and p7R sequence. RT-PCR analysis with primer pairs A and C showed only one band of ~1 kb (FIG. 8B, lane 3) as expected from this splicing event.

As a control, total RNA isolated from plants developed for the construct, P9LGp7C, was taken for RT-PCR using the primers pairs (A and B). A major 3.2 kb fragment of general structure (L-GUS-p7-CAT) was generated as expected (data not presented). RT-RCR analysis of total RNA from untransformed plants (Samsun NN) showed no PCR product (FIG. 8B, Lane 4).

EXAMPLE 6

Processing of Cat-Protein from Dicistronic Construct in Transgenic Plants

Figure 9:
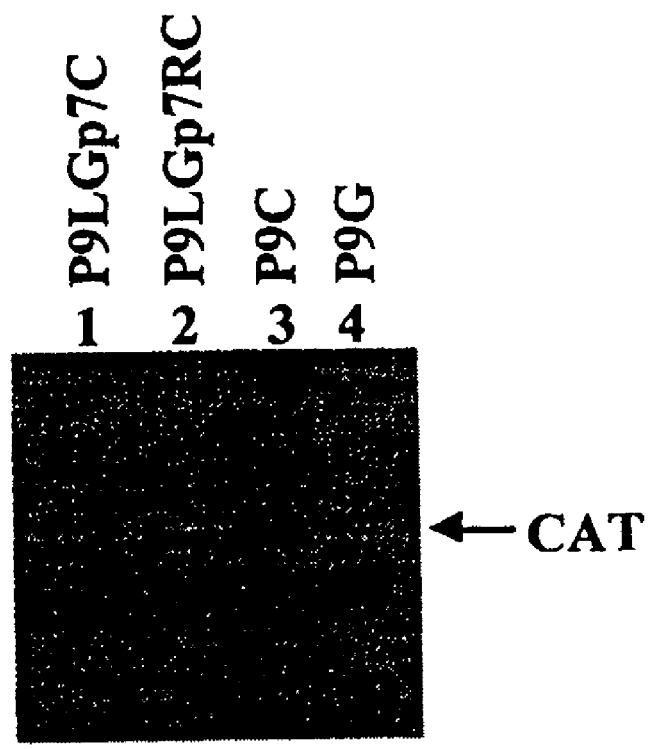
FIG. 9 is a Western blot analysis of the expression of the CAT gene ($2^{nd}$ cistron) from a dicistronic construct.

Western blot analysis of total soluble proteins extracted from leaves of transgenic plants developed with the dicistronic construct P9Lp7RC showed a band (FIG. 9, lane 2) of appropriate size for CAT-protein when it was probed with CAT-antisera. The band was also detected from the plants developed with P9C (CAT gene under P9 promoter) (FIG. 9, lane 3), but not from plants developed either with P9LGp7C or P9G (GUS gene under P9 promoter). It clearly established that the CAT gene is processed properly from the dicistronic construct to generate CAT protein of appropriate size.

REFERENCES

Maiti, I. B., Murphy, J. F., Shaw, J. G. and Hunt, A. G. (1993) Plant that express a potyvirus proteinase genes are resistant to virus infection. Proc Nad Acad Sci USA 90: 6110–6114.

Maiti, I. B. and Shepherd, R. J. (1998) Isolation and expression analysis of peanut chlorotic streak caulimovirus (PC1SV) full-length transcript (FLt) promoter in transgenic plants. Biochem, Biophys Res Commun 244: 440–444.

Maiti, I. B., Gowda, S., Kiernan, J., Ghosh, S. K. and Shepherd, R. J. (1997) Promoter/leader deletion analysis and plant expression vectors with the figwort mosaic virus (FMV) full length transcript (FLt) promoter containing single and double enhancer domains. Transgenic Research 6:143–156.

Maiti, I. B., Richins, R. D. and Shepherd, R. J. (1998) Gene expression regulated by gene VI of caulimovirus: trans-activation of downstream genes of transcripts by gene VI of peanut chlorotic streak virus in transgenic tobacco. Virus Research 57: 113–124.

Richins, R. D. 1994. Complete nucleotide sequence of the peanut chlorotic streak virus (PC1SV) genome: DNA EMBL Data Library GenBank Accession No. U13988

Reddy, D. V. R., Richins, R. D., Rajeshwari, R., Iizuka, N., Manohar, S. K. and Shepherd, R. J. (1993) Peanut chlorotic streak virus, a new caulimovirus infecting peanuts (*Arachis hypogaea*) in India. Phytopathology 83: 129–133.

4. The expression cassette of claim 2 further comprising a termination sequence operatively linked downstream of the polynucleotide sequence encoding the polypeptide.

5. The expression cassette of claim 4 wherein the termination sequence is a Rbcs E9 sequence.

6. A polycistronic expression cassette comprising a plant promoter operatively linked to SEQ ID NO: 1, which is operatively linked to a first nucleotide sequence encoding a first polypeptide, which is operatively linked to SEQ ID NO:

What is claimed is:

1. An expression cassette comprising a plant promoter operatively linked to SEQ ID NO: 1, which is operatively linked to SEQ ID NO: 2.

2. The expression cassette of claim 1 further comprising a polynucleotide sequence encoding a polypeptide or peptide operatively linked downstream of SEQ ID NO: 2.

3. The expression cassette of claim 1 wherein the plant promoter is a P9 promoter.

2, which is operatively linked to a second nucleotide sequence encoding a second polypeptide.

7. The polycistronic expression cassette of claim 6 wherein the second polynucleotide sequence is operatively linked downstream to a second copy of SEQ ID NO: 2, which is operatively linked downstream to a third nucleotide sequence encoding a third polypeptide.

8. The polycistronic expression cassette of claim 6 wherein the first polynucleotide sequence encodes a different polypeptide than the second polynucleotide sequence.

9. The polycistronic expression cassette of claim 7 wherein the first polynucleotide sequence, second polynucleotide sequence and third polynucleotide sequence each independently encode different polypeptides.

10. The polycistronic expression cassette of claim 6 or 7 further comprising a termination sequence operatively linked to the 3' end of the expression cassette.

11. The polycistronic cassette of claim 6 or 7 wherein the promoter is a P9 promoter.

12. The polycistronic expression cassette of claim 11 wherein the termination sequence is a Rbcs E9 sequence.

13. A polycistronic expression cassette comprising a plant promoter operatively linked to SEQ ID NO: 1, which is operatively linked to SEQ ID NO: 2, which is operatively linked to a first polynucleotide encoding a first polypeptide, which is operatively linked downstream to a second copy of SEQ ID NO: 2, which is operatively linked downstream to a second polynucleotide encoding a second polypeptide.

14. The polycistronic expression cassette of claim 13 further comprising a 3'-termination sequence.

15. The polycistronic expression cassette of claim 14 wherein the termination sequence is a Rbcs E9 sequence.

16. The polycistronic expression cassette of claim 13 wherein the promoter is a P9 promoter.

17. A transgenic plant, transgenic plant tissue, transgenic plant cell, or transgenic seed comprising the polycistronic expression cassette of any one of claims 6, 7 or 13.

18. A method of expressing one or more peptides or polypeptides in a plant, plant cells, plant tissue, or seeds comprising:
   transforming the plant, plant cells, plant tissue, or seeds with an expression cassette of any one of claims 2, 6, 7, or 13 and
   expressing the polypeptide or polypeptides encoded by the expression cassette.

19. The polycistronic expression cassette of claim 13, 14, 15 or 16 wherein the second polynucleotide encoding a second polypeptide is operatively linked downstream to a third copy of SEQ ID NO:2, which is operatively linked downstream to a third polynucleotide encoding a third polypeptide.

20. A transgenic plant, transgenic plant tissue, transgenic plant cell, or transgenic seed comprising the polycistronic expression cassette of claim 19.

21. A method of expressing one or more peptides or polypeptides in a plant, plant cells, plant tissue, or seeds comprising:
   transforming the plant, plant cells, plant tissue, or seeds with an expression cassette of claim 19 and
   expressing the polypeptide or polypeptides encoded by the expression cassette.

* * * * *